(12) United States Patent
Bochner et al.

(10) Patent No.: US 7,745,421 B2
(45) Date of Patent: Jun. 29, 2010

(54) METHODS AND COMPOSITIONS FOR TREATING DISEASES AND DISORDERS ASSOCIATED WITH SIGLEC-8 EXPRESSING CELLS

(75) Inventors: Bruce S. Bochner, Lutherville, MD (US); Ronald L. Schnaar, Columbia, MD (US)

(73) Assignee: The Johns Hopkins University, Baltimore, MD (US)

( * ) Notice: Subject to any disclaimer, the term of this patent is extended or adjusted under 35 U.S.C. 154(b) by 417 days.

(21) Appl. No.: 11/597,336

(22) PCT Filed: May 24, 2005

(86) PCT No.: PCT/US2005/018165

§ 371 (c)(1),
(2), (4) Date: Oct. 31, 2007

(87) PCT Pub. No.: WO2005/116088

PCT Pub. Date: Dec. 8, 2005

(65) Prior Publication Data

US 2008/0139485 A1 Jun. 12, 2008

Related U.S. Application Data

(60) Provisional application No. 60/574,331, filed on May 25, 2004, provisional application No. 60/624,378, filed on Nov. 2, 2004.

(51) Int. Cl.
*A61K 31/715* (2006.01)
(52) U.S. Cl. .............................. 514/54; 514/23; 514/25
(58) Field of Classification Search ....................... None
See application file for complete search history.

(56) References Cited

OTHER PUBLICATIONS

Hemmerich DDT (2001), vol. 6, pp. 27-35.*
Jain et al. J. Am. Chem. Soc. (1994), vol. 116, pp. 12123-12124.*
Komba, et al., "Synthesis of sialyl Le$^x$ ganglioside analogues sulfated at C-6 of either the galactose or N-acetylglucosamine residues, and at both of the galactose and N-acetylglucosamine residues: probes for clarifying the real carbohydrate ligand of L-selection[1]," *Carbohydrate Research*, (285), 1996, pp. C1-C8.
Dai, et al., "Matrix-assisted laser desorption ionization mass spectrometry for the analysis of monosulfated oligosaccharides", *Carbohydrate Research*, (304), 1997, pp. 1-9.

* cited by examiner

*Primary Examiner*—Patrick T Lewis
(74) *Attorney, Agent, or Firm*—Peter F. Corless; Colleen McKiernan; Edwards Angell Palmer & Dodge LLP

(57) ABSTRACT

The invention provides therapeutic methods and compositions for the prevention and treatment of Siglec-8 associated diseases and disorders such as asthma and allergic reactions. In particular, the invention provides methods and compositions for the prevention and treatment of diseases and disorders associated with Siglec-8 expressing cells in humans, as well as other animals, through the administration of one or more novel, carbohydrate-based compounds.

16 Claims, 7 Drawing Sheets

Figure 5
A.
B.
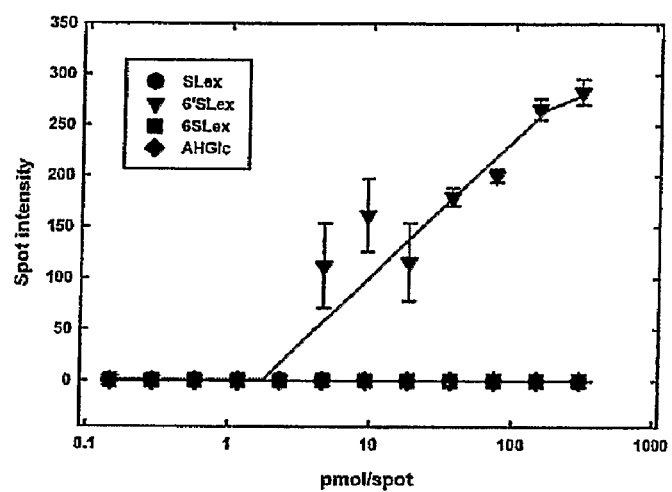

METHODS AND COMPOSITIONS FOR TREATING DISEASES AND DISORDERS ASSOCIATED WITH SIGLEC-8 EXPRESSING CELLS

PRIORITY

The present application claims priority to U.S. Provisional Application Nos. 60/574,331, filed May 25, 2004 and 60/624,378, filed Nov. 2, 2004.

GOVERNMENT SUPPORT

This work, in part, was funded by grant AI41472 from the National Institutes of Health.

FIELD OF THE INVENTION

The invention relates to methods and compositions useful in the treatment of disorders or diseases associated with Siglec-8 expressing cells, including asthma and other allergic diseases. Preferred methods and compositions of the invention comprise use of one or more novel, carbohydrate-based chemical compounds to treat a mammal suffering from or susceptible to such disorders.

BACKGROUND OF THE INVENTION

Siglecs (sialic acid-binding immunoglobulin-like lectins) are a recently designated family of cell surface molecules that are a subset of the immunoglobulin (Ig) gene superfamily (Crocker, P. R., and Varki, A. (2001) *Immunology* 103, 137-145; Crocker, P. R., and Varki, A. (2001) *Trends Immunol.* 22, 337-342; Crocker, P. R. (2002) *Curr Opin Struct Biol* 12, 609-615). Siglecs differ from traditional Ig superfamily members in several ways. While their extracellular domains contain a variable number of C2-set Ig domains, unlike other Ig superfamily members, Siglecs possess an N-terminal V-set Ig domain that binds sialylated structures (May, A. P., Robinson, R. C., Vinson, M., Crocker, P. R., and Jones, E. Y. (1998) *Mol Cell* 1, 719-728; Yamaji, T., Teranishi, T., Alphey, M. S., Crocker, P. R., and Hashimoto, Y. (2002) *J Biol Chem* 277, 6324-6332; Zaccai, N. R., Maenaka, K., Maenaka, T., Crocker, P. R., Brossmer, R., Kelm, S., and Jones, E. Y. (2003) *Structure (Camb)* 11, 557-567; Alphey, M. S., Attrill, H., Crocker, P. R., and van Aalten, D. M. (2003) *J Biol Chem* 278, 3372-3377; Dimasi, N., Moretta, A., Moretta, L., Biassoni, R., and Mariuzza, R. A. (2004) *Acta Crystallogr D Biol Crystallogr* 60, 401-403). In addition, Siglec cytoplasmic domains typically contain multiple tyrosine residues, including some with consensus immunoreceptor tyrosine-based inhibitory motifs (ITIMs). This suggests that Siglecs possess signal transduction activity. Direct evidence of signaling has already been shown for several human Siglecs (Falco, M., Biassoni, R., Bottino, C., Vitale, M., Sivori, S., Augugliaro, R., Moretta, L., and Moretta, A. (1999) *J. Exp. Med.* 190, 793-802; Mingari, M. C., Vitale, C., Romagnani, C., Falco, M., and Moretta, L. (2001) *Immunol. Rev.* 181, 260-268; Whitney, G., Wang, S., Chang, H., Cheng, K. Y., Lu, P., Zhou, X. D., Yang, W. P., McKinnon, M., and Longphre, M. (2001) *Eur. J. Biochem.* 268, 6083-6096; Nicoll, G., Avril, T., Lock, K., Furukawa, K., Bovin, N., and Crocker, P. R. (2003) *Eur J Immunol* 33, 1642-1648; Ikehara, Y., Ikehara, S. K., and Paulson, J. C. (2004) *J Biol Chem*).

Siglec-8 (alternate name: SAF-2, sialoadhesin family-2) was discovered by CD33 homology screening of expressed sequence tag sequences from a cDNA library made from a human eosinophil cDNA library (Kikly, K. K., Bochner, B. S., Freeman, S., Tan, K. B., Gallagher, K. T., D'Alessio, K., Holmes, S. D., Abrahamson, J., Hopson, C. B., Fischer, E. I., Erickson-Miller, C. L., Tachimoto, H., Schleimer, R. P., and White, J. R. (2000) *J. Allergy Clin. Immunol.* 105, 1093-1100; Floyd, H., Ni, J., Cornish, A. L., Zeng, Z., Liu, D., Carter, K. C., Steel, J., and Crocker, P. R. (2000) *J. Biol. Chem.* 275, 861-866). Highest levels of homology were found between Siglec-8 and Siglec-3 (49%), Siglec-5 (42%) and Siglec-7 (68%), with virtually all of the homology due to similarities in the extracellular and transmembrane regions. Subsequently, a splice variant of Siglec-8, termed Siglec-8L, containing an identical extracellular domain but a longer cytoplasmic tail possessing two tyrosine-based motifs, was discovered from human genomic DNA (Foussias, G., Yousef, G. M., and Diamandis, E. P. (2000) *Biochem Biophys Res Commun* 278, 775-781; Yousef, G. M., Ordon, M. H., Foussias, G., and Diamandis, E. P. (2002) *Gene* 286, 259-270). Additional experiments, using monoclonal antibodies, revealed that Siglec-8 was not only expressed on the surface of eosinophils, but on basophils and mast cells as well (Kikly, K. K., Bochner, B. S., Freeman, S., Tan, K. B., Gallagher, K. T., D'Alessio, K., Holmes, S. D., Abrahamson, J., Hopson, C. B., Fischer, E. I., Erickson-Miller, C. L., Tachimoto, H., Schleimer, R. P., and White, J. R. (2000) *J. Allergy Clin. Immunol.* 105, 1093-1100) and the existence of both the Siglec-8 and Siglec-8L isoforms was verified in human eosinophils, basophils and mast cells (Aizawa, H., Plitt, J., and Bochner, B. S. (2002) *J. Allergy Clin. Immunol.* 109, 176; Nutku, E., Aizawa, H., Tachimoto, H., Hudson, S. A., and Bochner, B. S. (2004) in *Allergy Frontiers and Futures, Proceedings of the 24th Symposium of the Collegium Internationale Allergologicum* (Bienenstock, J., Ring, J., and Togias, A. G., eds), pp. 130-132, Hogrefe and Huber, Cambridge Mass.). Most recently it was demonstrated that antibody crosslinking of Siglec-8 on human eosinophils induced caspase-dependent apoptosis in vitro (Nutku, E., Aizawa, H., Hudson, S. A., and Bochner, B. S. (2003) *Blood* 101, 5014-5020).

The search for Siglec ligands remains rather complex. Many of the Siglecs recognize α2-3- and α2-6-linked sialic acids (Freeman, S. D., Kelm, S., Barber, E. K., and Crocker, P. R. (1995) *Blood* 85, 2005-2012; Brinkman-Van der Linden, E. C., and Varki, A. (2000) *J. Biol. Chem.* 275, 8625-8632) while others bind to other sialylated structures. For example, Siglec-1 has been shown to bind the highly glycosylated surface protein CD43 (van den Berg, T. K., Nath, D., Ziltener, H. J., Vestweber, D., Fukuda, M., van Die, I., and Crocker, P. R. (2001) *J. Immunol.* 166, 3637-3640), the epithelial mucin MUC-1 (Nath, D., Hartnell, A., Happerfield, L., Miles, D. W., Burchell, J., Taylor-Papadimitriou, J., and Crocker, P. R. (1999) *Immunology* 98, 213-219) and sialylated lipopolysaccharide (Jones, C., Virji, M., and Crocker, P. R. (2003) *Mol Microbiol* 49, 1213-1225). Among a panel of glycans tested, Siglec-3 showed enhanced binding to a multivalent form of sialyl-Tn (NeuAcα2-6GalNAc) disaccharides (Brinkman-Van der Linden, E. C., Angata, T., Reynolds, S. A., Powell, L. D., Hedrick, S. M., and Varki, A. (2003) *Mol Cell Biol* 23, 4199-4206). Siglec-7 binds to GD3, LSTb, sialyl Lewis$^a$ and NeuAcα2-8NeuAc, while Siglec-9 preferentially binds GD1a and LSTc (Rapoport, E., Mikhalyov, I., Zhang, J., Crocker, P., and Bovin, N. (2003) *Bioorg Med Chem Lett* 13, 675-678; Miyazaki, K., Ohmori, K., Izawa, M., Koike, T., Kumamoto, K., Furukawa, K., Ando, T., Kiso, M., Yamaji, T., Hashimoto, Y., Suzuki, A., Yoshida, A., Takeuchi, M., and Kannagi, R. (2004) *Cancer Res* 64, 4498-4505). For Siglec-8, it has been shown that red blood cell rosettes are formed with Siglec-8, and neuramimidase treatment alters rosette formation (Kikly, K. K., Bochner, B. S., Freeman, S., Tan, K. B., Gallagher, K. T., D'Alessio, K., Holmes, S. D., Abrahamson, J., Hopson, C. B., Fischer, E. I., Erickson-Miller, C. L., Tachimoto, H., Schleimer, R. P., and White, J. R. (2000) *J. Allergy Clin. Immunol.* 105, 1093-1100; Floyd, H., Ni, J., Cornish, A. L., Zeng, Z., Liu, D., Carter, K. C., Steel, J., and Crocker, P. R. (2000) *J. Biol. Chem.* 275, 861-866). Specific structures shown to bind Siglec-8 include forms of sialic acid linked α2-3 or α2-6 to Galβ1-4GlcNAc (Floyd, H., Ni, J., Cornish, A. L., Zeng, Z., Liu, D., Carter, K. C., Steel, J., and Crocker, P. R. (2000) *J. Biol. Chem.* 275, 861-866). In a more comprehensive evaluation of binding specificities, ten Siglec-Ig chimeras were screened for binding to 28 different sialoside-streptavidin-alkaline phosphatase probes, and a wide range of binding patterns were observed, but there was no clear binding preference for Siglec-8 (Blixt, O., Collins, B. E., van den Nieuwenhof, I. M., Crocker, P. R., and Paulson, J. C. (2003) *J Biol Chem* 278, 31007-31019).

Pharmacological activation of Siglec-8 would be expected to deplete eosinophils, basophils, and mast cells from the body and/or reduces their activation level. This kind of pharmacologic effect may be used for treatment of diseases including asthma, allergic diseases, atopic dermatitis, hypereosinophilic syndromes, mastocytosis, leukemias, sinusitis, nasal polyposis, urticaria and anaphylaxis.

Given the prevalence of asthma and other allergic conditions, there remains a need for effective prophylactic and therapeutic treatment of these disorders, in particular, those related disorders associated with Siglec-8 expressing cells in a subject.

SUMMARY OF THE INVENTION

The present invention relates to novel, carbohydrate-based chemical structures that bind to the cell surface protein Siglec-8, which is expressed by human eosinophils, basophils and mast cells. Siglec-8 binding reduces the activity and/or viability of these cells. When bound (e.g. by specific antibodies), Siglec-8 signals eosinophils to rapidly undergo apoptosis, or programmed cell death. Because basophils and mast cells also express Siglec-8, it has been inferred that a similar apoptosis response occurs upon Siglec-8 binding to ligands. Other inhibitory signals can be transduced by Siglec-8, such as inhibition of histamine release from basophils and mast cells or inhibition of eosinophil degranulation. Since these cells mediate pathology in asthma and allergic diseases, molecules based on the disclosed carbohydrate structure can reduce the numbers and/or level of activation of these cells and alleviate symptoms. Other diseases caused by increased numbers or activation of these cell types (e.g., asthma, allergic diseases, atopic dermatitis, hypereosinophilic syndromes, mastocytosis, leukemias, lymphomas, nasal polyposis, urticaria and anaphylaxis.) can be amenable to treatment using such molecules.

The invention provides a compound represented by the formula (Formula I):

in which A is a sialic acid residue or an analog thereof; B is a galactose residue or an analog thereof, and is substituted with an anionic moiety at the 6-position; C is an N-acetylglucosamine residue or an analog thereof; D is a fucose residue or an analog thereof; and R is H, or together with the O atom to which it is attached, forms an aglycone; or a pharmaceutically acceptable salt thereof.

The term "aglycone" is art-recognized and as used herein refers to a moiety (typically a non-sugar moiety) that is joined to a carbohydrate moiety through an acetal linkage at C-1 of the carbohydrate (e.g., C-1 of residue "C" in Formula I, above). Examples of aglycones include —OCH$_3$, —OCH$_2$CH$_3$, —O—(C$_1$-C$_6$-alkyl) (which may be substituted or unsubstituted), and the like.

In certain preferred embodiments, A is a sialic acid residue. In other preferred embodiments, A is a sialic acid analog or mimetic represented by the structure:

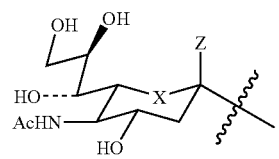

in which X is O or CH$_2$ and Z is an anionic group selected from the group consisting of carboxylate, sulfate, sulfonate, phosphate, phosphonate and hydroxamate, and the wavy line indicates the point of attachment to the galactose residue or analog thereof.

In certain embodiments, B is a 6-Y-galactose residue, in which Y is an anionic group; in preferred embodiments, Y is an anionic group selected from the group consisting of carboxylate, sulfate, sulfonate, phosphate, phosphonate and hydroxamate.

In certain embodiments, C is an N-acetylglucosamine residue. In other embodiments, C is an N-acetylglucosamine analog or mimetic represented by the formula:

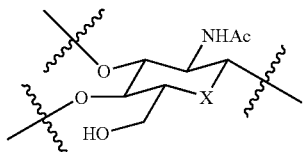

in which X is O or CH$_2$.

In certain preferred embodiments, D is a fucose residue.

In certain preferred embodiments, R, together with the O atom to which it is attached, forms an aglycone represented by the structure —O—(CH$_2$)$_3$—NH—CO(CH$_2$)$_5$NH-M, where M is a hydrogen or amide linkage (e.g., —C(O)—(C$_1$-C$_6$-alkyl), —C(O)-aryl (e.g., phenyl), which may be substituted or unsubstituted, —C(O), and the like).

In another embodiment, the invention provides a compound represented by the formula (Formula II):

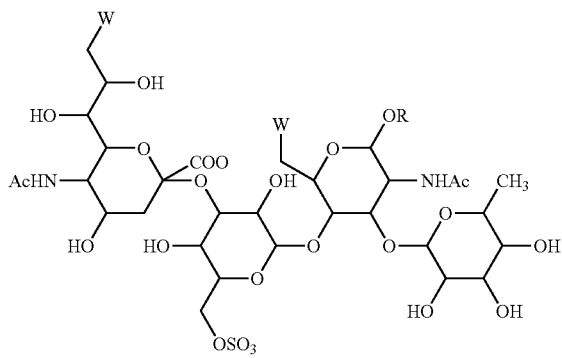

in which R is H or together with the O atom to which it is attached forms an aglycone; and W is independently for each occurrence F, OH, or O—U—V; wherein U is absent or is —C(O)— or —C(O)O—, and V is $C_1$-$C_4$ alkyl or aryl;

or a pharmaceutically acceptable salt thereof.

In certain preferred embodiments, W is —OH for each occurrence.

In another embodiment, the invention provides a compound represented by the formula (Formula III):

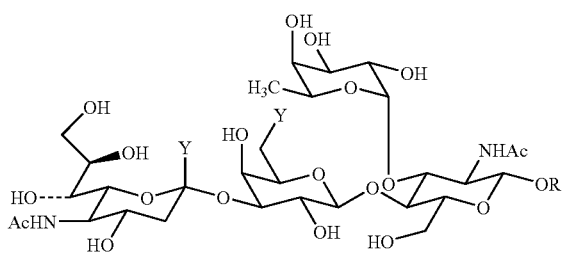

in which R is H or together with the O atom to which it is attached forms an aglycone; and Y is independently for each occurrence an anionic group selected from the group consisting of carboxylate, sulfate, sulfonate, phosphate, phosphonate and hydroxamate; or a pharmaceutically acceptable salt thereof.

In certain preferred embodiments, R, together with the O atom to which it is attached, forms is an aglycone represented by the structure —O—(CH$_2$)$_3$—NH—CO(CH$_2$)$_5$NH-M, where M is a hydrogen or amide linkage, (e.g., —C(O)—(C$_1$-C$_6$-alkyl), —C(O)-aryl (e.g., phenyl), which may be substituted or unsubstituted, —C(O), and the like).

In a most preferred embodiment, the invention provides the compound NeuAcα2-3(6-O-sulfo)Galβ1-4(Fucα1-3)GlcNAcβ-O—(CH$_2$)$_3$—NH—CO(CH2)$_5$NH$_2$; or a pharmaceutically acceptable salt thereof.

In any of the preceding embodiments, preferred compounds bind to the Siglec-8 protein.

In another aspect, the invention provides a pharmaceutical composition comprising any of the compounds of the invention, together with a pharmaceutically acceptable solvent.

Analogs and derivatives include mimetics that resemble a mono- or polysaccharide of interest. For example, one or more of the monosaccharide moieties of NeuAcα2-3(6-O-sulfo)Galβ1-4(Fucα1-3)GlcNAc can be replaced with isosteric moieties having different properties (e.g., replacing the N-acetylglucosamine residue with an N-acetylgalactosamine residue). Synthetic compounds that mimic the conformation and desirable features of a particular polysaccharide ligand, e.g., a tetrasaccharide, and preferably avoid at least some undesirable features (such as low binding affinity, short half-life in vivo, and the like) of the original tetrasaccharide of interest, are referred to herein as a "mimetics".

Preferred therapeutic methods of the invention in general comprise administering an effective amount of one or more of the above described novel, carbohydrate-based compounds to a subject (e.g., a mammal, particularly human) or cells (e.g. mammalian cells particularly human in need thereof), e.g. a subject or cells that are suffering from or susceptible to a disease or disorder associated with activation of Siglec-8 on Siglec-8 expressing cells, including but not limited to eosinophils, basophils and mast cells.

The invention also includes pharmaceutical compositions that comprise one or more of the above described unique, carbohydrate-based compounds optionally admixed with a pharmaceutically acceptable carrier and optionally packaged together with instructions (e.g. written) for use of the composition for a condition as disclosed herein.

Other and further aspects, features and advantages of the present teachings will be apparent from the following description of the various embodiments of the present teachings given for the purpose of disclosure.

BRIEF DESCRIPTION OF THE FIGURES

FIG. 5, panels a and c, illustrate further verification of Siglec-8 Ig binding specificity using immobilized glycans on glass slides. Aminoalkyl glycans (as indicated, AH-Glc=aminohexylglucoside) were covalently spotted (as indicated, 0.15-300 µmol/spot) on an activated glass slide; Binding was visualized using Siglec-8 Ig fusion protein precomplexed with fluorescent anti-human Fc antibody as described in Materials and Methods; Binding was only seen with 6'-sulfo-sLe$^x$ (Panel A) at concentrations of 4.7 pmol/spot and above; In Panel B, replicate spot fluorescence intensities were averaged and displayed with error bars representing means±SD from a single experiment using quadruplicate spots.

DETAILED DESCRIPTION OF THE INVENTION

It is understood that this invention is not limited to the particular materials and methods described herein. It is also to be understood that the terminology used herein is for the purpose of describing particular embodiments and is not intended to limit the scope of the present invention which will be limited only by the appended claims. As used herein, the singular forms "a", "an", and "the" include plural reference unless the context clearly dictates otherwise. For example, a reference to "leucocytes" includes a plurality of cells known to those skilled in the art.

Unless defined otherwise, all technical and scientific terms used herein have the same meanings as commonly understood by one of ordinary skill in the art to which this invention belongs. All publications mentioned herein are cited for the purpose of describing and disclosing the models, protocols and reagents which are reported in the publications and which might be used in connection with the invention. Nothing herein is to be construed as an admission that the invention is not entitled to antedate such disclosure by virtue of prior invention.

I: Relationship Between Unique Glycans and Siglec-8 Expressing Cells

The Consortium for Functional Glycomics (http://www-.functionalglycomics.org) was funded as a large research initiative by the National Institutes of General Medical Sciences to facilitate research efforts focused on improving the understanding of the mechanisms by which glycan-binding proteins (GBPs) mediate cell communication. The Consortium is integrating the efforts of several scientific Cores and participating investigators to achieve these aims. Among several cores is the Protein-Carbohydrate Interaction Core H and Carbohydrate Synthesis Protein Expression Core D. These Cores have developed a high-throughput screening platform for identifying GBP-ligand interactions using a streptavidin/biotin-based glycan array containing ~180 different glycan structures immobilized as biotinylated glycosides on a 384-well streptavidin-coated plate. This was developed as an expansion of previous efforts (Blixt, O., Collins, B. E., van den Nieuwenhof, I. M., Crocker, P. R., and Paulson, J. C. (2003) *J Biol Chem* 278, 31007-31019) and in conjunction with the Carbohydrate Synthesis Core D to determine the glycan-binding specificity of GBPs. A secondary analysis method was also used to quantitate the relative binding affinities of candidate ligands by surface plasmon resonance. Here we report that these and other approaches have been used to determine that Siglec-8 is a highly specific lectin, binding preferentially to the sLe$^x$ structure bearing an additional sulfate ester on the galactose 6-hydroxyl, namely NeuAcα2-3 (6-O-sulfo)Galβ1-4-[Fucα1-3]GlcNAc, also referred to in the literature as 6'-sulfo-sLe$^x$, a structure closely related to 6-sulfo-sLe$^x$, a candidate ligand for L-selectin.

Figure 1:
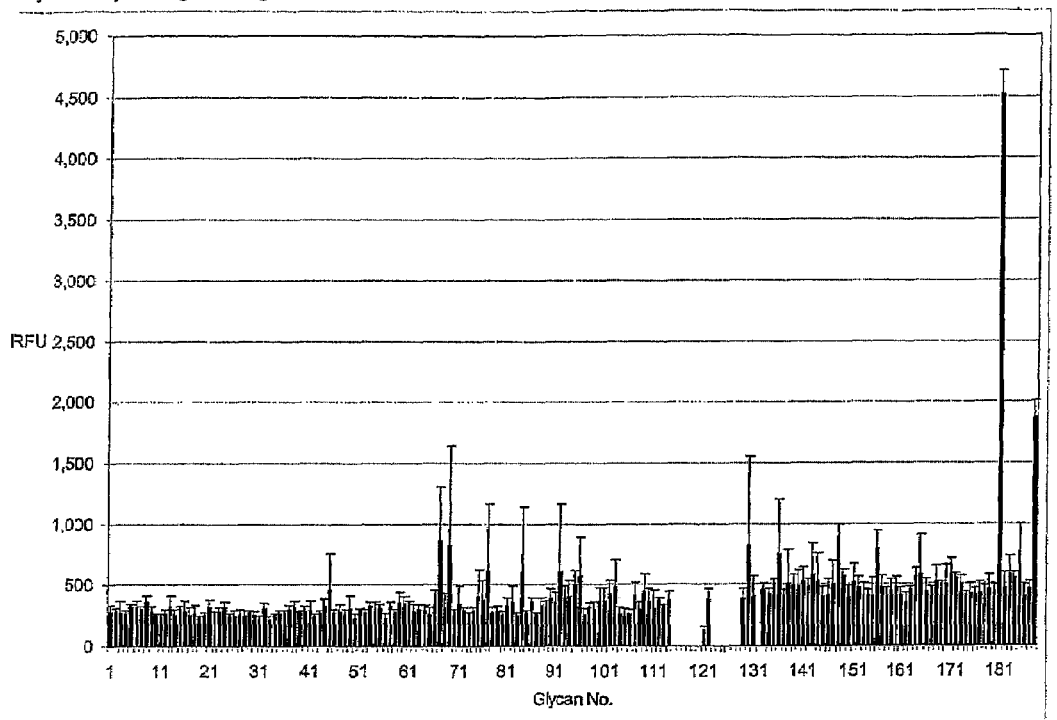
FIG. 1 depicts the results from the Siglec-8-Ig glycan binding array analysis; A total of 172 structures were screened for binding along with positive and negative controls as described in Materials and Methods; Error bars represent mean±SD replicate determinations from a single experiment; Note that ligand #181 (6'-sulfo-sLe$^x$) stands out among all the others for binding activity.
Figure 2:
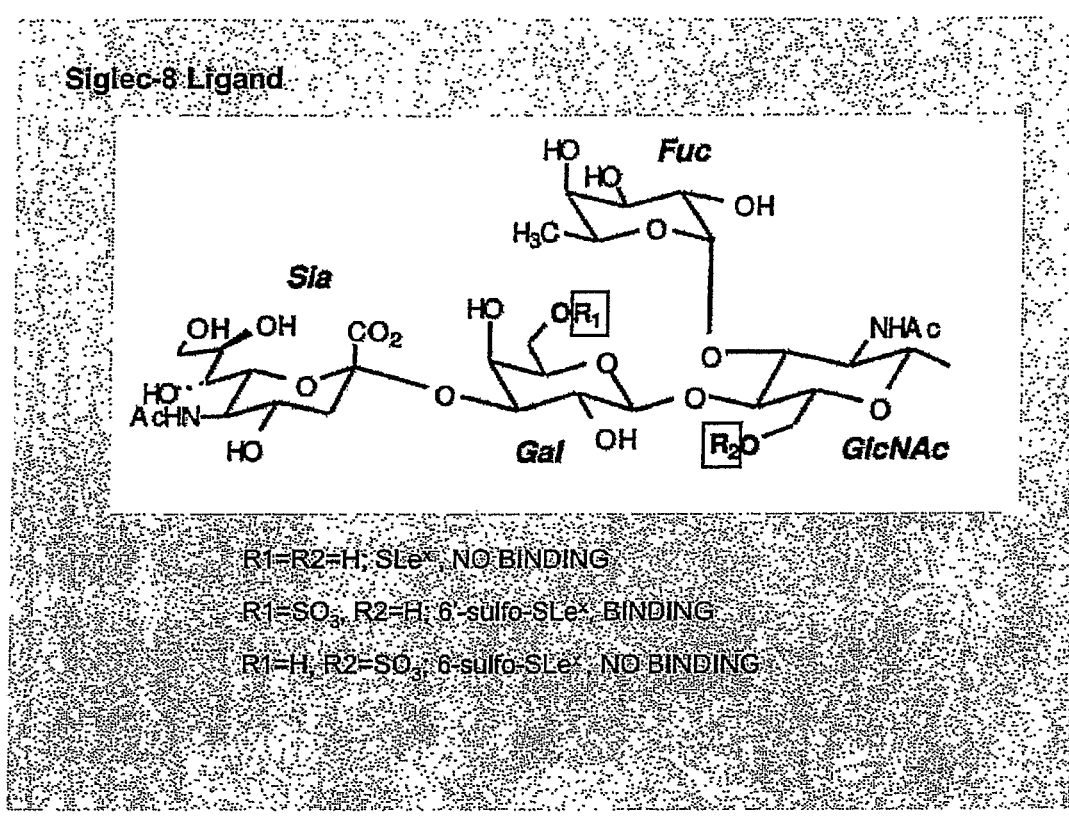
FIG. 2. is a representation of structures of glycans used to verify specificity of Siglec-8-Ig binding; These included 6-sulfo-sLe$^x$, 6'-sulfo-sLe$^x$, and sLe$^x$.
Figure 3A:
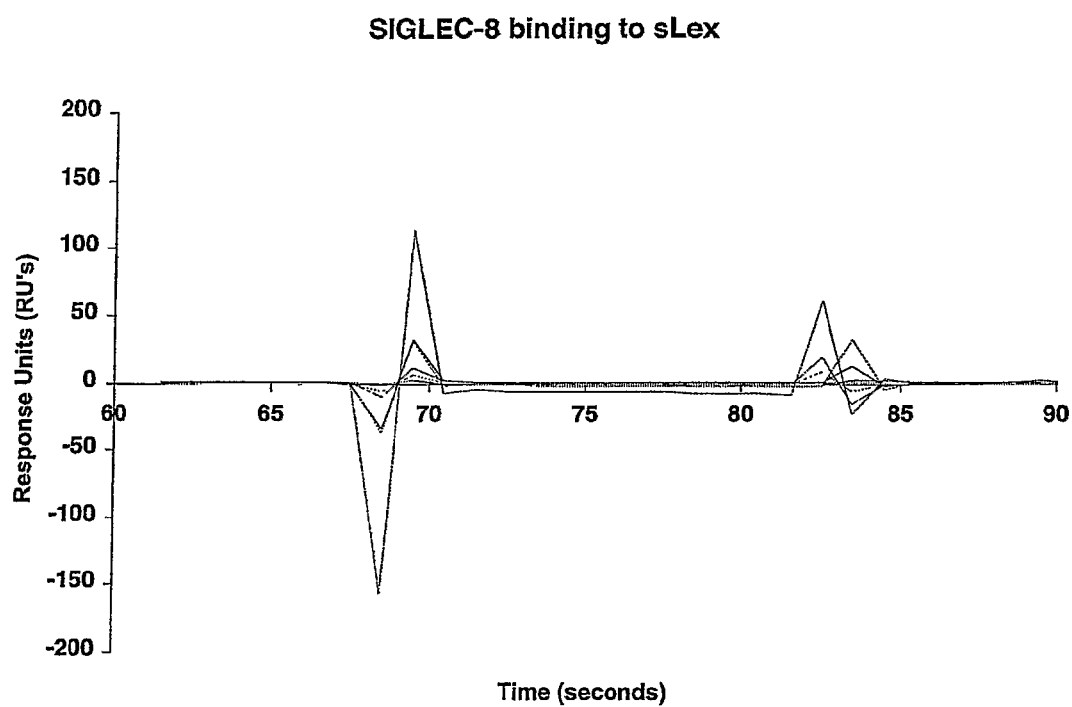
FIG. 3, panels a, b and c illustrate the specificity of Siglec-8 binding as assessed using SPR; No binding of Siglec-8 Ig-was detected to sLe$^x$ (Panel A) or 6-sulfo-sLe$^x$, (Panel B), while reproducible binding was detected to 6'-sulfo-sLe$^x$ (Panel C).
Figure 3B:
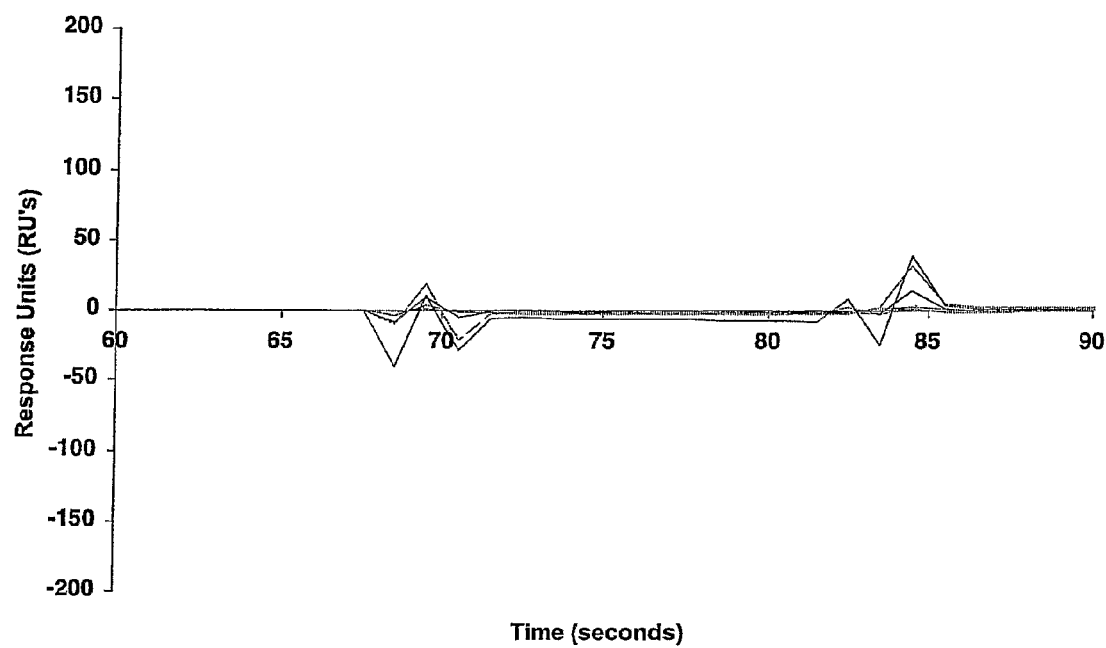
Figure 3C:
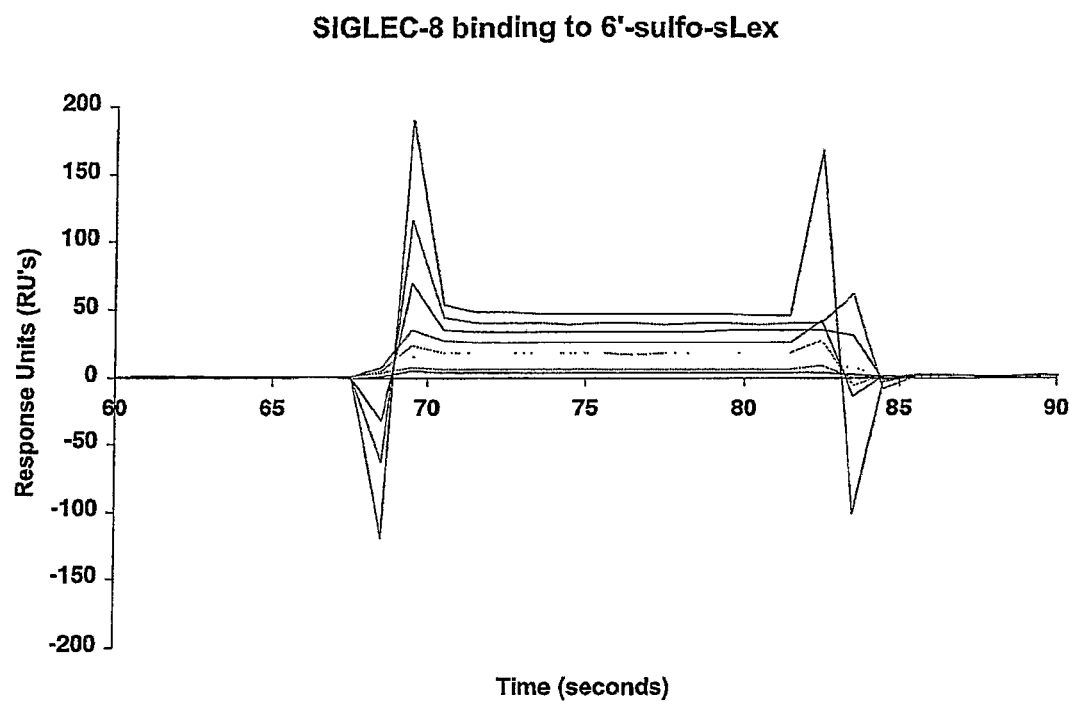
Figure 4:
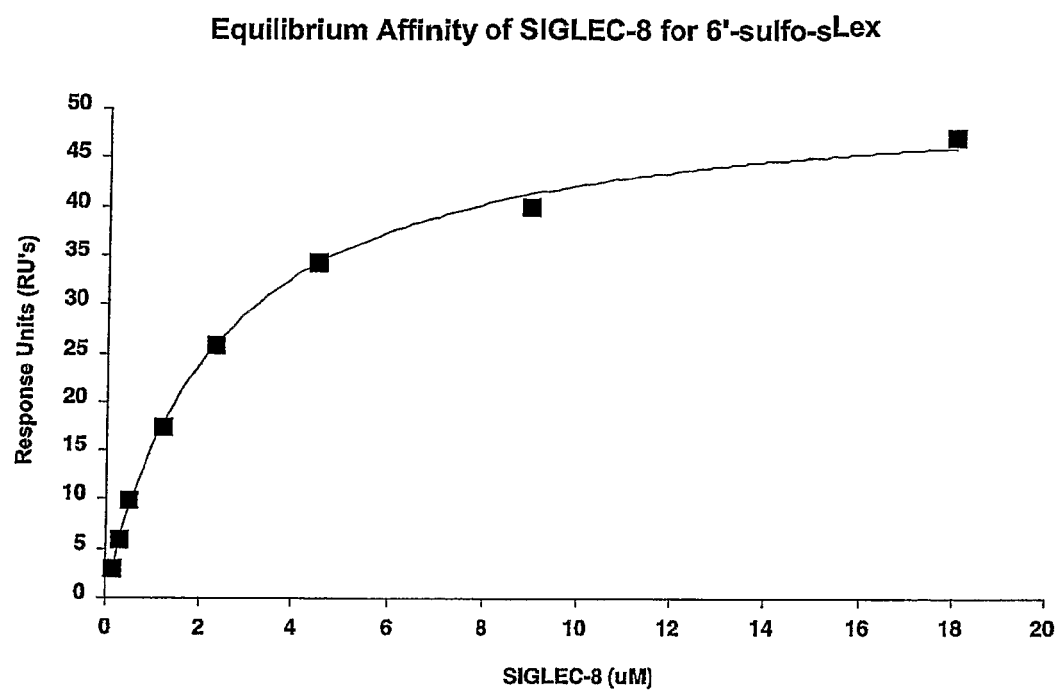
FIG. 4. graphically illustrates the affinity of Siglec-8 Ig binding to 6'-sulfo-sLe$^x$ as measured by SPR; Based on three replicate analyses, the dissociation constant (Kd) was 2.2-2.3 µM.

Using a glycan array assembled by the Consortium for Functional Glycomics, 172 structures were screened for their ability to bind to Siglec-8 Ig fusion protein. By far the greatest binding was seen with ligand #181, which is 6'-sulfo-sLe$^x$ (FIGS. 1 and 2). Specificity was subsequently verified using SPR and a separate assay using immobilized glycans (FIGS. 3-5). These three separate methods confirmed the specificity to be 6'-sulfo-sLe$^x$ and not closely related structures because Siglec-8-Ig fusion protein failed to bind to unsulfated sLe$^x$ as well as the closely related structure 6-sulfo-sLe$^x$. To our knowledge, this represents the first published example of the successful use of this glycan ELISA-based array, which is much more extensive than those previously published (Blixt, O., Collins, B. E., van den Nieuwenhof, I. M., Crocker, P. R., and Paulson, J. C. (2003) *J Biol Chem* 278, 31007-31019). In addition, the specificity of binding, with reasonably high affinity (Kd: 2.3 µM) to only one out of 172 ligands tested, suggests that 6'-sulfo-sLe$^x$ is a strong candidate for being a Siglec-8 ligand. The only other structure in the glycan array to show binding to Siglec-8 above background was ligand #188, which is a mixture of biantennary N-glycans from Wehi-3 cell supernatants. It is not known whether this supernatant contains 6'-sulfo-sLe$^x$. While the specificity of binding of 6'-sulfo-sLe$^x$ for Siglec-8 versus other human Siglecs has not yet been explored, this is the first time this ligand has been suspected to bind to any of the Siglecs. The functional mouse ortholog for Siglec-8 is Siglec-F (Zhang, J. Q., Biedermann, B., Nitschke, L., and Crocker, P. R. (2004) *Eur J Immunol* 34, 1175-1184), and according to the Consortium website, Siglec-F also selectively binds 6'-sulfo-sLe$^x$. Additional experiments using a Siglec-G-Ig fusion protein failed to show specific binding to 6'-sulfo-sLe$^x$, providing some degree of selectivity of binding for Siglec-8 (also according to the Consortium website). Additionally, it remains to be determined what role various components of 6'-sulfo-sLe$^x$, such as fucose, play in binding. Finally, there are no known receptors for the structure, although initial studies suggested that 6'-sulfo-sLe$^x$ might serve as an L-selectin ligand (Tsuboi, S., Isogai, Y., Hada, N., King, J. K., Hindsgaul, O., and Fukuda, M. (1996) *J Biol Chem* 271, 27213-27216). However, subsequent studies found that 6-sulfo-sLe$^x$ rather than 6'-sulfo-sLe$^x$ was a preferred ligand (Sanders, W. J., Katsumoto, T. R., Bertozzi, C. R., Rosen, S. D., and Kiessling, L. L. (1996) *Biochemistry* 35, 14862-14867; Bowman, K. G., Hemmerich, S., Bhakta, S., Singer, M. S., Bistrup, A., Rosen, S. D., and Bertozzi, C. R. (1998) *Chem Biol* 5, 447-460; Bistrup, A., Bhakta, S., Lee, J. K., Belov, Y. Y., Gunn, M. D., Zuo, F. R., Huang, C. C., Kannagi, R., Rosen, S. D., and Hemmerich, S. (1999) *J Cell Biol* 145, 899-910; Hemmerich, S., Bistrup, A., Singer, M. S., van Zante, A., Lee, J. K., Tsay, D., Peters, M., Carminati, J. L., Brennan, T. J., Carver-Moore, K., Leviten, M., Fuentes, M. E., Ruddle, N. H., and Rosen, S. D. (2001) *Immunity* 15, 237-247).

Synthesis of 6'-sulfo-sLe$^x$ requires the presence of specific sulfotransferases in the Golgi apparatus of cells. Based on the known family of human Golgi-associated sulfotransferases (GSTs) (Hemmerich, S., Lee, J. K., Bhakta, S., Bistrup, A., Ruddle, N. R., and Rosen, S. D. (2001) *Glycobiology* 11, 75-87; Grunwell, J. R., and Bertozzi, C. R. (2002) *Biochemistry* 41, 13117-13126; Kusche-Gullberg, M., and Kjellen, L. (2003) *Curr Opin Stiuct Biol* 13, 605-611), at least GST-1 (also known as keratan sulfate galactose 6-O sulfotransferase (KSGal6ST) and carbohydrate sulfotransferase I (CHST-1)), which is known to sulfate galactose residues linked to N-acetyl glucosamine, would likely be involved in the synthesis of 6'-sulfo-sLe$^x$ (FIG. 2). These genes are located on chromosome 11p11.1-11.2, and studies report rather broad tissue distribution of CHST-1 (Mazany, K. D., Peng, T., Watson, C. E., Tabas, I., and Williams, K. J. (1998) *Biochim Biophys Acta* 1407, 92-97; Li, X., and Tedder, T. F. (1999) *Genomics* 55, 345-347), although KSGal6ST has been reportedly expressed predominantly in brain tissue and to a lesser degree in skeletal muscle (Fukuta, M., Inazawa, J., Torii, T., Tsuzuki, K., Shimada, E., and Habuchi, O. (1997) *J Biol Chem* 272, 32321-32328). Methods such as immunohistochemistry would be useful in identifying tissue localization of 6'-sulfo-sLe$^x$ expression, but to date, there are no antibody reagents that can distinguish 6'-sulfo-sLe$^x$ from 6-sulfo-sLe$^x$ (Mitsuoka, C., Sawada-Kasugai, M., Ando-Furui, K., Izawa, M., Nakanishi, H., Nakamura, S., Ishida, H., Kiso, M., and Kannagi, R. (1998) *J Biol Chem* 273, 11225-11233). Previous studies with monoclonal antibodies suggest that cross-linking of Siglec-8 induces apoptosis on cells that express Siglec-8, such as human eosinophils (Nutku, E., Aizawa, H., Hudson, S. A., and Bochner, B. S. (2003) *Blood* 101, 5014-

5020), so it is tempting to speculate that expression of Siglec-8 ligand in the central nervous system may be a way to eliminate inflammatory cells that have infiltrated the CNS.

In summary, a Siglec-8-Ig chimeric protein was screened for binding to 172 different glycan structures immobilized as biotinylated glycosides. Among these, avid binding was detected to a single defined glycan: NeuAcα2-3(6-O-sulfo) Galβ1-4-[Fucα1-3]GlcNAc, also referred to in the literature as 6'-sulfo-sLe$^x$.

We now provide new therapeutic agents and methods that can decrease the number of eosinophil, basophil and mast cells, as well as the release of histamine and other mediators from these cells effectively in vivo II. Novel, Carbohydrate-Based Compounds:

Structures capable of binding and activating Siglec-8 include compounds containing a galactose (Gal) or other sugar bearing a sulfate ester or other anionic constituent at its 6-hydroxyl or another hydroxyl alone or as part of an oligosaccharide structure that contains a terminally linked sialic acid (NeuAc), a fucose (Fuc) and/or an N-acetylglucosamine (GlcNAc) residue, and is part of the specific oligosaccharide NeuAcα2-3(6-O-sulfo)Galβ1-4(Fucα1-3) GlcNAc. The oligosaccharide or related compound is in glycosidic linkage to an aglycone of the structure O(CH$_2$)$_3$NH—CO(CH$_2$)$_5$NH-Biotin or to other aglycones or without an aglycone (free reducing end). The compounds can exist as a sodium salt or other cationic salts such as potassium, lithium, ammonium, calcium, etc. Preferred salts are pharmaceutically acceptable salts. The phrase "pharmaceutically acceptable" refers to those compound of the inventions of the present invention, compositions containing such compounds, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds are effective in suppressing the activities of eosinophils, basophils and/or mast cells in diseases in which those cells are active.

The present invention provides a compound represented by the formula

in which A is a sialic acid residue or an analog thereof; B is a galactose residue or an analog thereof, and is substituted with an anionic moiety at the 6-position; C is an N-acetylglucosamine residue or an analog thereof; D is a fucose residue or an analog thereof; and R is H or together with the O atom to which it is attached, forms an aglycone; or a pharmaceutically acceptable salt thereof.

In certain preferred embodiments, A is a sialic acid residue. In other preferred embodiments, A is a sialic acid analog or mimietic represented by the structure:

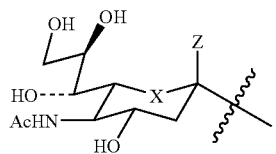

in which X is O or CH$_2$ and Z is an anionic group selected from the group consisting of carboxylate, sulfate, sulfonate, phosphate, phosphonate and hydroxamate, and the wavy line indicates the point of attachment to the galactose residue or analog thereof.

In certain embodiments, B is a 6-Y-galactose residue, in which Y is an anionic group; in preferred embodiments, Y is an anionic group selected from the group consisting of carboxylate, sulfate, sulfonate, phosphate, phosphonate and hydroxamate.

In certain embodiments, C is an N-acetylglucosamine residue. In other embodiments, C is an N-acetylglucosamine analog or mimietic represented by the formula:

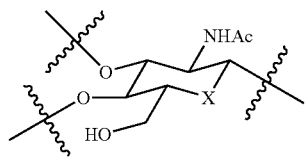

in which X is O or CH$_2$.

In certain preferred embodiments, D is a fucose residue.

In certain preferred embodiments, R is an aglycone represented by the structure —O—(CH$_2$)$_3$—NH—CO(CH2)$_5$NH-M, where M is a hydrogen or amide linkage (e.g., —C(O)—(C$_1$-C$_6$-alkyl), —C(O)-aryl (e.g., phenyl), which may be substituted or unsubstituted, —C(O), and the like).

In another embodiment, the invention provides a compound represented by the formula (Formula II):

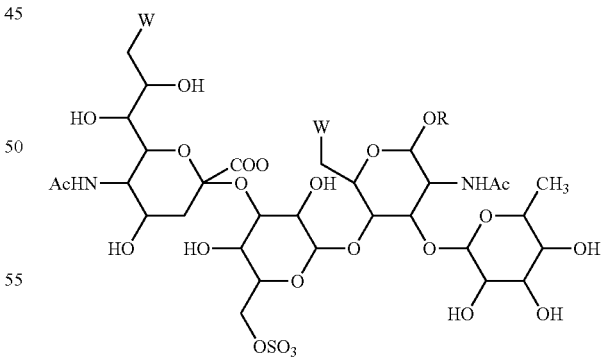

in which R is H or an aglycone; and

W is independently for each occurrence F, OH, or O—U—V;
wherein U is absent or is —C(O)— or —C(O)O—, and V is C$_1$-C$_4$ alkyl or aryl (e.g., substituted or unsubstituted phenyl);

or a pharmaceutically acceptable salt thereof.

In certain preferred embodiments, W is —OH for each occurrence.

In another embodiment, the invention provides a compound represented by the formula (Formula III):

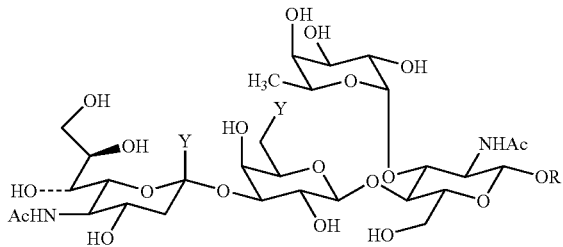

in which R is H, or, together with the O atom to which it is attached, forms an aglycone; and Y is independently for each occurrence an anionic group selected from the group consisting of carboxylate, sulfate, sulfonate, phosphate, phosphonate and hydroxamate; or a pharmaceutically acceptable salt thereof.

In certain preferred embodiments, R (together with the O atom to which it is attached) is an aglycone represented by the structure —O—$(CH_2)_3$—NH—CO$(CH_2)_5$NH.

In a most preferred embodiment, the invention provides the compound NeuAcα2-3(6-O-sulfo)Galβ1-4(Fucα1-3)GlcNAcβ-O—$(CH_2)_3$—NH—CO$(CH_2)_5$NH-M, where M is a hydrogen or amide linkage (e.g., —C(O)—($C_1$-$C_6$-alkyl), —C(O)-aryl (e.g., phenyl), which may be substituted or unsubstituted, —C(O), and the like); or a pharmaceutically acceptable salt thereof.

In any of the preceding embodiments, preferred compounds bind to Siglec-8 protein.

In another aspect, the invention provides a pharmaceutical composition comprising any of the compounds of the invention, together with a pharmaceutically acceptable solvent.

Analogs and derivatives include mimetics that resemble a mono- or polysaccharide of interest. For example, one or more of the monosaccharide moieties of NeuAcα2-3(6-O-sulfo)Galβ1-4(Fucα1-3)GlcNAc can be replaced with an analogous moiety or moieties (e.g., isosteric moieties) having different properties (e.g., by replacing the N-acetylglucosamine residue with an N-acetylgalactosamine moiety, or replacing a fucose residue with a carbocyclic analog of fucose, e.g., replacing the ring oxygen of fucose with a $CH_2$ moiety) but retaining useful biological activity. Synthetic compounds or moieties (e.g., structural or functional analogs) that mimic the conformation and desirable features of a particular polysaccharide ligand (or portion thereof), e.g., a tetrasaccharide or terasaccharide derivative, and preferably avoid at least some undesirable features (such as low binding affinity, short half-life in vivo, and the like) of the original tetrasaccharide of interest, are referred to herein as a "mimetics".

II. Methods of Treatment

As discussed above, the invention provides therapeutic methods and compositions for the prevention and treatment of diseases and disorders associated with Siglec-8 expressing cells such as asthma and allergic reactions. Siglec-8 expressing cells, include but are not limited to, eosinophils, basophils, mast cells and Langerin cells (dendritic cells in the skin). In particular, the invention provides methods and compositions for the prevention and treatment of Siglec-8 associated diseases and disorders in humans as well as other animals through the administration of one or more novel, carbohydrate-based compounds.

Molecules containing the key elements or based upon the disclosed structures above are novel drugs that reduce asthmatic or allergic symptoms by reducing the numbers and/or level of activation of eosinophils, basophils and/or mast cells. In addition, other diseases associated with increased numbers or activation of these same cell types (e.g., hypereosinophilic syndromes, mastocytosis, leukemias, urticaria, Churg-Strauss syndrome, eosinophilic esophagitis, eosinophilic gastroenteritis, nasal polyposis) may be therapeutic targets of such molecules.

In one embodiment, the present invention contemplates a method of treatment, comprising: a) providing: i) a mammalian patient, particularly human, who is either at risk for or who has symptoms of a disease or disorder associated with Siglec-8 expressing cells, ii) one or more of the novel, carbohydrate-based compounds described above, and; b) administering the one or more of those compounds to the patient.

The present invention is also not limited by the degree of benefit achieved by the administration of novel, carbohydrate-based compounds described above. For example, the present invention is not limited to circumstances where all symptoms are eliminated. In one embodiment, administering of one or more of these compounds reduces the number or severity of symptoms of a disease or disorder associated with Siglec-8 expressing cells (e.g., the degree by which the asthmatic and/or allergic reaction is reduced). In another embodiment, administering of one or more of these compounds may delay the onset of symptoms.

As mentioned above, the indications for which the administration of one or more of the novel, carbohydrate-based compounds can be used include in particular asthma and allergic diseases, e.g., treatment (including amelioration, reduction, elimination or cure of etiology or symptoms) or prevention (including substantial or complete restriction, prophylaxis or avoidance) of the following: hypereosinophilic syndromes, mastocytosis, leukemias, urticaria, Churg-Strauss syndrome, eosinophilic esophagitis, eosinophilic gastroenteritis and nasal polyposis The treatment methods and compositions of the invention also will be useful for treatment of mammals other than humans, including for veterinary applications such as to treat horses and livestock e.g. cattle, sheep, cows, goats, swine and the like, and pets such as dogs and cats.

One or more novel, carbohydrate-based compounds may be administered as a "cocktail" formulation with other therapeutics, i.e. coordinated administration of one or more compounds of the invention together with one or more other active therapeutics, such as one or more other agents used to treat asthma, and/or one or more agents to treat allergic reactions. For instance, a novel, carbohydrate-based compound may be administered in coordination with corticosteroids or bronchodilators for asthma, or agents used for treatment of allergic reactions (e.g. adrenalin, and the like).

III. Pharmaceutical Compositions

The novel, carbohydrate-based compounds described above (also referred to herein as "active compounds") of the invention can be incorporated into pharmaceutical compositions suitable for administration. Such compositions typically comprise the active compounds and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. As discussed above, supplementary active compounds can also be incorporated into the compositions.

A pharmaceutical composition of the invention is formulated to be compatible with its intended route of administration. Examples of routes of administration include, but are not limited to, parenteral, e.g., intravenous, intradermal, intramuscular, intraosseous, subcutaneous, oral, intranasal, inhalation, transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). The composition preferably is sterile and should be fluid to the extent that easy syringability exists. The compositions suitably should be stable under the conditions of manufacture and storage and preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., NeuAc$\alpha$2-3(6-O-sulfo) Gal$\beta$1'-4(Fuc$\alpha$1-3)GlcNAc$\beta$-O—(CH$_2$)$_3$—NH—CO(CH$_2$)$_5$NH-M, where M is a hydrogen or amide linkage) in a therapeutically effective or beneficial amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. Suitable oral compositions may be e.g. enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as hydroxyfluoroalkane (HFA), or a nebulizer. Alternatively, intranasal preparations may be comprised of dry powders with suitable propellants such as HFA.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially e.g. from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the $LD_{50}$ (the dose lethal to 50% of the population) and the ED50 (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

Data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The pharmaceutical compositions can be included in a container, pack, or dispenser together with instructions (e.g. written) for administration, particularly such instructions for use of the active agent to treat against a disorder or disease as disclosed herein, including diseases or disorders associated with Siglec-8 expressing cells.

The following non-limiting examples are illustrative of the invention. All documents mentioned herein are incorporated herein by reference in their entirety.

EXAMPLES

This invention is further illustrated by the following examples which are provided for the purpose of illustration only and the invention should in no way be construed as being limited to these examples but rather should be construed to encompass any and all variations which become evident as a result of the teaching provided herein. The contents of all references, patents, and published patent applications cited throughout this application, as well as the figures, are incorporated herein by reference.

Exemplification

Materials and Methods Used in the Examples

ABBREVIATIONS

Siglec Sialic acid binding immunoglobulin-like lectin
NeuAc Sialic acid
Gal Galactose
Fuc Fucose
GlcNAc N-acetylglucosamine
$sLe^x$ Sialyl Lewis X
ITIM immunoreceptor tyrosine-based inhibitory motif
GBP glycan-binding protein
PBS phosphate buffered saline
SPR surface plasmon resonance
Streptavidin SA
GST Golgi-associated sulfotransferase
KSGal6ST keratan sulfate galactose 6-O sulfotransferase
CHST carbohydrate sulfotransferase
Siglec-8-Ig Chimera The extracellular domain of Siglec-8 was inserted in frame with a Factor Xa cleavage site and the Fc portion of human $IgG_1$, expanded in electroporated CHOEA1 cells, and then purified from supernatants (final concentration: 2.4 mg/ml) using Protein A Sepharose as previously described (Kikly, K. K., Bochner, B. S., Freeman, S., Tan, K. B., Gallagher, K. T., D'Alessio, K., Holmes, S. D., Abrahamson, J., Hopson, C. B., Fischer, E. I., Erickson-Miller, C. L., Tachimoto, H., Schleimer, R. P., and White, J. R. (2000) *J. Allergy Clin. Immunol.* 105, 1093-1100).

Glycomics Consortium Screening for Siglec-8 Ligands

Biotinylated glycosides (Korchagina, E., and Bovina, N. V. (1992) *Bioorg Khim* 18, 283-298) were coated in replicates of n=3 or n=4 on streptavidin-coated microtiter plates (Pierce Reacti-Bind™ NeutrAvidin™ Coated High Binding Capacity Black 384-Well Plates, Product #15513, Rockford, Ill.). Each well was incubated overnight at 4° C. with 30 pmol/well of glycoside in 25 ul phosphate buffered saline (PBS), pH 7.4. The plates were washed three times with 100 ul PBS using an automated plate washer (Molecular Devices, Sunnyvale, Calif.) and stored sealed at 4° C. in 25 ul/well PBS with 0.1% azide until use. Prior to assay, the plates were washed three times with 100 ul/well wash buffer (20 mM Tris-HCl pH 7.4, 150 mM NaCl, 2 mM $CaCl_2$, 2 mM $MgCl_2$ and 0.05% Tween 20). A stock solution of Siglec-8-g (30 ug/ml) was added to each well in 25 ul binding buffer (wash buffer plus 1% BSA) and incubated at room temperature for one hour. The plates were washed three times with 100 ul/well wash buffer and incubated for one hour with 25 ul/well goat anti-human IgG-Alexa 488 (Molecular Probes, Cat. No. A11013, Eugene, Oreg.) at 5 ug/ml in binding buffer. The plates were washed and read in 25 ul wash buffer on a Victor 2™ 1420 Multilabel Counter (PerkinElmer Life Sciences, Fremont, Calif.) at excitation 485/emission 535. The glycosides probed are listed in Table 1. The current version of the Consortium glycan array can be viewed at: http://www.functionalglycomics.org/static/consortium/resources/resourcecoreh2.shtml

TABLE 1

Listing of the glycan structures that were screened by Core H of the
Consortium for Functional Glycomics using the Glycan Array.

GLYCANS

| No. | Glycan - spacer | Glycan name and/or trivial name |
|---|---|---|
| 02 | α-D-Glc-Sp2 | α-D-glucose |
| 03 | β-D-Glc-Sp2 | β-D-glucose |
| 04 | α-D-Gal-Sp2 | α-D-galactose |
| 05 | β-D-Gal-Sp2 | β-D-galactose |
| 06 | 3-O-Su-Galβ-Sp2 | β-D-galactose-3-sulfate |
| 07 | β-GlcNAc-Sp2 | β-N-acetyl-D-glucosamine |
| 08 | α-GalNAc-Sp2 | α-N-acetyl-D-galactosamine ($T_n$) |
| 09 | β-GalNAc-Sp2 | β-N-acetyl-D-galactosamine |
| 10 | α-D-Man-Sp2 | α-D-mannose |
| 11 | 6-H$_2$PO$_3$Manα-Sp2 | α-D-mannose-6-phosphate |
| 12 | α-L-Fuc-Sp2 | α-L-fucose |
| 13 | α-Neu5Ac-Sp2 | α-N-acetylneuraminic acid |
| 14 | α-L-Rhα-Sp2 | α-L-rhamnose |
| 15 | Glcα1-4Glcβ-Sp2 | maltose |
| 16 | Galβ1-4Glcβ-Sp1 | lactose |
| 17 | Galβ1-3Galβ-Sp2 | Galβ1-3Gal |
| 18 | Galα1-4GlcNAc-Sp2 | Galα1-4GlcNAc |
| 19 | Galβ1-3GlcNacβ-Sp1 | Le$^c$ |
| 20 | Galβ1-3GlcNacβ-Sp2 | T$_{ββ}$ |
| 21 | Galβ1-4GlcNAcβ-Sp1 | LacNAc |
| 22 | GalNAcβ1-4GlcNAcβ-Sp2 | Lac-di-NAc |
| 23 | Galα1-3(Fucα2)Galβ-Sp2 | B$_m$ |
| 24 | Fucα2Galβ1-3(Fucα1-4)GlcNAcβ-Sp2 | Le$^b$ |
| 25 | Galβ1-4(Fucα1-3)GlcNAc-Sp1 | Le$^x$ |
| 26 | GalNAcβ1-4(Fucα1-3)GlcNAc-Sp1 | Fucα1-3-Lac-di-NAc |
| 27 | Galβ1-3GlcNAcβ-Sp2 | Le$^c$ |
| 28 | Fucα2Galβ1-3GlcNAcβ1-3Galβ1-4Glcβ-Sp5 | Lacto-N-fucopentose 1 |
| 29 | Galβ1-3(Fucα1-4)GlcNAc-Sp2 | Le$^a$ |
| 30 | Galα1-4Galβ1-4Glcβ-Sp1 | P$^k$ |
| 31 | Galα1-4Galβ1-4GlcNacβ-Sp1 | P$_1$ |
| 32 | Galβ1-4GlcNacβ1-3Galβ1-4Glcβ-Sp1 | LNnT |
| 33 | GlcNacβ1-3Galβ1-4Glcβ-Sp1 | LNT-2 |
| 34 | Galβ1-4GlcNAcβ1-3Galβ1-4GlcNAcβ-Sp1 | LN2 |
| 35 | Galβ1-4GlcNAcβ1-3Galβ1-4GlcNAcβ1-3Galβ1-4GlcNAcβ-Sp1 | LN3 |
| 36 | Neu5Acα2-3Galβ1-4Glcβ-Sp1 | GM3 |
| 37 | Neu5Gcα2-3Galβ1-4Glcβ-Sp1 | GM3 (Gc) |
| 38 | Neu5Acα2-3Galβ1-4GlcNAcβ-Sp1 | 3'SLN |
| 39 | Neu5Acα2-3Galβ1-3GlcNAcβ-Sp1 | 3'-SiaLe$^c$ |
| 40 | Neu5Gcα2-3Galβ1-4GlcNAcβ-Sp1 | 3'SLN (Gc) |
| 41 | Neu5Acα2-6Galβ1-4GlcNAcβ-Sp1 | 6'SLN |
| 42 | Neu5Gcα2-6Galβ1-4GlcNAcβ-Sp1 | 6'SLN (Gc) |
| 43 | Neu5Acα2-8Neu5Acα2-3Galβ1-4Glcβ-Sp1 | GD3 |
| 44 | KDNα2-3Galβ1-4GlcNAcβ-Sp1 | 3'KDNLe$^c$ |
| 45 | KDNα2-3Galβ1-3GlcNAcβ-Sp1 | 3'KDNLN |
| 46 | Manα1-3(Manα1-6)Man[α + β]-Sp2 | Man$_3$ |
| 47 | GalNAcα1-P2-Sp1 | T$_n$ |
| 48 | Galβ1-3GalNAcα1-P2-Sp1 | Core 1 |
| 49 | Galβ1-3(GlcNAcβ1-6)GalNAcα1-P2-Sp1 | Core 2 |
| 50 | Galβ1-3(Galβ1-4GlcNAcβ1-6)GalNAcα1-P2-Sp1 | β-galactosylated Core 2 |
| 51 | Galβ1-3(Galβ1-4[Fucα1-3]GlcNAcβ1-6)GalNAcα1-T.P1-Sp1 | Le$^x$ on Core 2 |
| 52 | Galβ1-3(Galα1-3Galβ1-4GlcNacβ1-6)GalNAcα1-T.P1-Sp1 | α-galactose on Core 2 |
| 53 | Galβ1-3(Neu5Acα2-3Galβ1-4GlcNAcβ1-6)GalNAcα1-T.P1-Sp1 | α1-3Neu5Ac on Core 1 |
| 54 | Galβ1-3(Neu5Acα2-3Galβ1-4[Fucα1-3]GlcNAcβ1-6)GalNAcα1-T.P1-Sp1 | α1-3Neu5Ac on Core 1 of Core 2 |
| 55 | Neu5Acα2-3Galβ1-3GalNacα1-T.P1-Sp1 | α1-3Neu5Ac on Core 1 on β-galactosylated Core 2 |
| 56 | Neu5Acα2-3Galβ1-3(GlcNAcβ1-6)GalNAcα1-T.P1-Sp1 | α1-3Neu5Ac on Core 1 on α-galactose on Core 2 |
| 57 | Neu5Acα2-3Galβ1-3(Galβ1-4GlcNAcβ1-6)GalNAcα1-T.P1-Sp1 | α1-3Neu5Ac on Core 1 with Lex on Core 2 |
| 58 | Neu5AcGalβ1-3(Galα1-3Galβ1-4GlcNAcβ1-6)GalNAcα1-T.P1-Sp1 | α1-3Neu5Ac on Core 2 |
| 59 | Neu5Acα2-3Galβ1-3(Galβ1-4[Fucα1-3]GlcNAcβ1-6)GalNAcα1-T.P1-Sp1 | sLe$^x$ on Core 2 |
| 60 | Neu5Acα2-3Galβ1-3(Neu5Acα2-3Galβ1-4GlcNAcβ1-6)GalNAcα1-T.P1-Sp1 | Disialyl Core 2 |
| 61 | Neu5Acα2-3Galβ1-3(Neu5Acα2-3Galβ1-4[Fucα1-3]GlcNAcβ1-6)GalNAcα1-T.P1-Sp1 | Disialyl Core 2 with sLex on Core 2 |
| 62 | 6-O-Su-GlcNAcβ-Sp2 | β-N-acetyl-D-glucosamine-6-sulfate |

TABLE 1-continued

| | | |
|---|---|---|
| 63 | 6-Su-GalNAcα-Sp2 | α-N-acetyl-D-galactosamine-6-sulfate |
| 64 | Galα1-3Galβ-Sp2 | $B_{di}$ |
| 65 | Galβ1-2Galβ-Sp2 | Gal2bGal |
| 66 | 3'-O-Su-Galβ1-4Glcβ-Sp2 | 3'-su-LacNAc |
| 67 | Galβ1-4(6-O-Su)GlcNAcβ-Sp2 | 6'-O-su-LacNAc |
| 68 | Gal α1-3GalNAcβ-Sp2 | $T_{on}$ |
| 69 | Galβ1-3GalNAcα-Sp2 | TF |
| 70 | 3'-O-Su-Galβ1-3GlcNAcβ-Sp2 | 3'-su-Le$^c$ |
| 71 | GlcNAcβ1-4GlcNAcβ-Sp2 | (GlcNAc)$_2$ |
| 72 | GlcNAcβ1-3GalNAcα-Sp2 | Core 3 |
| 73 | GalNAcα1-3GalNAcα-Sp2 | Fs-2 |
| 74 | Fucα2Galβ-Sp2 | $H_{di}$ |
| 75 | Fucα1-3GlcNAcβ-Sp2 | Fucα1-3GlcNAc |
| 76 | Fucα1-4GlcNAcβ-Sp2 | Fucα1-4GlcNAc, Le |
| 77 | Galα1-3(Fucα2)Galβ-Sp7 | $B_m$-long |
| 78 | Galβ1-4GlcNAcβ1-6GalNAcα-Sp2 | 6-LacNAc-$T_n$ |
| 79 | 3-O-Su-Galβ1-4(Fucα1-3)GlcNAcβ-Sp2 | 3'-O-su-Le$^x$ |
| 80 | GlcNAcβ1-3(GlcNAcβ1-6)GalNAcα-Sp2 | Core 4 |
| 81 | GalNAcα1-3(Fucα2)Galβ-Sp2 | $A_m$ |
| 82 | GalNAcα1-3(Fucα2)Galβ-Sp7 | $A_m$-long |
| 83 | Neu5Acα2-6Galβ1-4Glcβ-Sp3 | 6'-SL |
| 84 | Neu5Acα2-6(Galβ1-3)GalNAcα-Sp2 | 6'-SiaTF |
| 85 | Fucα2Galβ1-3GalNAcα-Sp2 | H (type 3) |
| 86 | Fucα2Galβ1-3GlcNAcβ-Sp2 | Le$^d$ (H type 1) |
| 87 | Fucα2Galβ1-4GlcNAcβ-Sp2 | H (type 2) |
| 88 | Fucα2Galβ1-4(Fucα1-3)GlcNAcβ-Sp2 | Le$^y$ |
| 89 | (Galβ1-4GlcNAcβ)$_2$-3,6-GalNAcα-Sp2 | 3,6-(LacNAc)$_2$T$_n$ |
| 90 | β-D-Glc-PAA | β-D-glucose |
| 91 | α-D-Gal-PAA | α-D-galactose |
| 92 | β-D-Gal-PAA | β-D-galactose |
| 93 | α-GalNAc-PAA | α-N-acetyl-D-galactosamine (T$_n$) |
| 94 | β-GalNAc-PAA | β-N-acetyl-D-galactosamine |
| 95 | Galβ1-4Glcβ-PAA | Lac |
| 96 | Galβ1-4GlcNAcβ-PAA | LacNAc |
| 97 | Galβ1-3GalNAcβ-PAA | T$_{bb}$ |
| 98 | GalNAcβ1-4GlcNAc-PAA | Lac-di-NAc |
| 99 | Manα1-3(Manα1-6)Man-PAA | Man$_3$ |
| 100 | Fucα2Galα1-3Galβ-PAA | B$_m$ |
| 101 | GlcNAcβ1-3Galβ1-4GlcNAcβ-Sp1 | GlcNAcβ1-3'LacNAc |
| 102 | Galβ1-4(Fucα1-3)GlcNAcβ1-4Galβ1-4(Fucα1-3)GlcNAcβ1-4Galβ1-4(Fucα1-3)GlcNAcβ-Sp1 | Tri-Le$^x$ |
| 103 | Galβ1-3(Fucα1-4)GlcNAcβ-Sp1 | Le$^a$ |
| 104 | Fucα1-2Galβ1-4Glcβ-Sp1 | 2'FL |
| 105 | Fucα1-2Galβ1-4GlcNAcβ1-3Galβ1-4GlcNAc-Sp1 | 2'F-Di-LN |
| 106 | Neu5Acα2-3Galβ1-4GlcNAcβ1-4Galβ1-4GlcNAcβ-Sp1 | 3'SiaDi-LN |
| 107 | Neu5Acα2-3(GalNAcβ1-4)Galβ1-4Glcβ-Sp1 | GM2 |
| 108 | Neu5Acα2-3Galβ1-4(Fucα1-3)GlcNAcβ-Sp1 | sLe$^x$ |
| 109 | Neu5Acα2-6Galβ1-4GlcNAcβ1-4Galβ1-4GlcNAcβ-Sp1 | 3'SiaDi-LN |
| 110 | Neu5Acα8Neu5Acα2-3(GalNAcβ1-4)Galβ1-4Glcβ-Sp1 | GD2 |
| 111 | Neu5Acα8Neu5Acα8Neu5Acα2-3Galβ1-4Glcβ-Sp1 | GD3 |
| 112 | GalNAcβ1-4GlcNAcβ1-4Manα1-6(GalNAcβ1-4GlcNAcβ1-4Manα1-3)Manβ1-4GlcNAcβ1-4GlcNAcβ-N-Sp1 | Bi-LDN (modified from human fibrinogen) |
| 113 | mixed glycans Man5-9-N-Sp1 | mixture of Man5-Man9 (from bovine pancreatic ribonuclease b) |
| 114 | Manα1-6(Manα1-3)Manα1-6(Manα1-3)Manβ1-4GlcNAcβ1-4GlcNAcβ-N-Sp1 | Man5 (from bovine pancreatic ribonuclease b) |
| 115 | Blank | Blank |
| 116 | Blank | Blank |
| 117 | Blank | Blank |
| 118 | Blank | Blank |
| 119 | Blank | Blank |
| 120 | Blank | Blank |
| 121 | Blank | Blank |
| 122 | Negative Control | No ligand + FITC-GBP + wahes |
| 123 | Background Control | Phosphate Buffered Saline |
| 124 | Positive Control 1 | FITC-RCA + Galβ1-4Glcβ-(16) |
| 125 | Positive Control 2 | FITC-SNA + Neu5Acα2-6Galβ1-4GlcNAcβ-(41) |
| 126 | Positive Control 3 | FITC-ConA + Manα1-3(Manα1-6) Man[a + b]-(46) |
| 127 | Blank | Blank |
| 128 | Blank | Blank |
| 129 | Manα1-6(Manα1-3)Manα1-6(Manα2Manα1-3)Manβ1-4GlcNAcβ1-4GlcNAcβ-N-Sp1 | Man6 (from bovine pancreatic ribonuclease b) |

TABLE 1-continued

| | | |
|---|---|---|
| 130 | Manα2Manα1-6(Manα1-3)Manα1-6(Manα2Manα1-3)Manβ1-4GlcNAcβ1-4GlcNAcβ-N-Sp1 | Man7 (from bovine pancreatic ribonuclease b) |
| 131 | Manα2Manα1-6(Manα1-3)Manα1-6(Manα2Manα2Manα1-3)Manβ1-4GlcNAcβ1-4GlcNAcβ-N-Sp1 | Man8 (from bovine pancreatic ribonuclease b) |
| 132 | Manα2Manα2Manα1-3(Manα2Manα1-3(Manα2Manα1-6)Manα1-6)Manβ1-4GlcNAcβ1-4GlcNAcβ-N-Sp1 | Man9 (from bovine pancreatic ribonuclease b) |
| 133 | Galβ1-4GlcNAcβ1-4Manα1-3(Galβ1-4GlcNAcβ1-4Manα1-6)Manα1-4GlcNAcβ1-4GlcNAcβ-N-Sp1 | As-Fibrinogen (bianfennary gal(2)) |
| 134 | Galα2Galβ-Sp2 | Galα2Gal |
| 135 | GalNAcα1-3Gal-Sp2 | $A_{di}$ |
| 136 | GlcNAcβ1-4GlcNAcβ-Sp2 | $(GlcNAc)_2$ |
| 137 | GlcNAcβ1-6GalNAcα-Sp2 | Core 6 |
| 138 | Galα1-3Galβ1-4GlcNAcβ-Sp2 | Galα1-3'LacNAc |
| 139 | Galβ1-4GlcNAcβ1-3GalNAcα-Sp2 | 3-LacNAc-$T_n$ |
| 140 | GlcNAcβ1-4GlcNAcβ1-4GlcNAcβ-Sp2 | chitotriose |
| 141 | GlcNAcβ1-6(Galβ1-3)GalNAcα-Sp2 | Core 2 |
| 142 | Fucα2Galβ1-3GalNAcβ-PAA | H (type 4) |
| 143 | Galβ1-4GlcNAcβ1-6(Galβ1-3)GalNAcα-Sp2 | 6-LacNAc-TF |
| 144 | Galβ1-4GalNAcβ1-4Galβ1-4Glcβ-Sp2 | GA1, asialo-GM1 |
| 145 | GlcNAcβ1-4GlcNAcβ1-4GlcNAcβ1-4GlcNAcβ-Sp3 | chitotetraose |
| 146 | Manα1-3(Manα1-6)Manβ1-4GlcNAcβ1-4GlcNAcβ-Sp2 | Man3-chitobiose |
| 147 | Neu5Acα2-3Gal-Sp2 | GM4 |
| 148 | Neu5Acα2-3GalNAcα-Sp2 | 3-SiaT$_n$ |
| 149 | Neu5Acα2-6Galβ-Sp2 | Neu5Ac6Gal |
| 150 | Neu5Acα2-6GalNAcα-Sp2 | SiaT$_n$ |
| 151 | Neu5Gcα6GalNAcα-Sp2 | α-Neu5Gc-$T_n$ |
| 152 | Neu5Acβ1-6GalNAcα-Sp2 | β-SiaT$_n$ |
| 153 | Neu5Acα2-3Galβ1-3GlcNAc-Sp2 | 3'-SiaLe$^c$ |
| 154 | Neu5Acα2-3(Neu5Acα2-6)GalNAcα-Sp2 | 3,6-SiaT$_n$ |
| 155 | Neu5Acβ1-6(Galβ1-3)GalNAcα-Sp2 | 6-SiabTF |
| 156 | Neu5Acα8Neu5Acα8Neu5Acα-Sp6 | $(Sia)_3$ |
| 157 | Neu5Acα2-3Galβ1-3(Neu5Acα2-6)GalNAcα-Sp2 | Siα2TF |
| 158 | 3-Su-GalNAcβ-Sp2 | GalNAc-3-O-sulfate |
| 159 | 6-O-Su-Galβ1-4Glcβ-Sp2 | 6'-O-su-LacNac |
| 160 | 6'-NeuAcα2-3Galβ1-4GlcNAcβ-Sp2 | 6'SLN |
| 161 | 3'-O-Su-Galβ1-3GalNAcα-Sp2 | 3'-O-su-TF |
| 162 | PAA | Control carrier |
| 163 | mixed glycans-N-Sp1 | mixed biantennary gal(0,1,2) core Fuc from bovine IgG |
| 164 | mixed glycans-N-Sp1 | mixed biantennary gal(1) core Fuc from bovine IgG |
| 165 | mixed glycans-N Sp1 | mixed biantennary gal(2) core Fuc from bovine IgG |
| 166 | Galα1-3GalNAcβ-Sp2 | $T_{\alpha\beta}$ |
| 167 | Galα1-3Galβ1-4(Fucα1-3)GlcNAcβ-Sp2 | αGalLe$^x$ |
| 168 | Galα1-3(Fucα2)Galβ1-4GlcNAcβ-Sp2 | B (type 2) |
| 169 | Galβ1-3GlcNAcβ1-3Galβ1-4Glcβ-Sp2 | LNT |
| 170 | GlcNAcβ1-4GlcNAcβ-Sp3 | $(GlcNAc)_2$ |
| 171 | GlcNAcβ1-2Galβ1-3GalNAcα-Sp2 | GlcNAcβ1-2'TF |
| 172 | GalNAcα1-3(Fucα2)Galβ1-4GlcNAcβ-Sp2 | A (type 2) |
| 173 | Neu5Acα2-Sp4 | α-N-acetylneuraminic acid |
| 174 | Neu5Acβ1-2-Sp4 | β-N-acetylneuraminic acid |
| 175 | Neu5Gcα-Sp2 | α-N-glycolylneuraminic acid |
| 176 | Neu5Gcβ-Sp2 | β-N-glycolylneuraminic acid |
| 177 | Neu5Acα2-3Galβ1-4GlcNAcβ-Sp2 | 3'SLN |
| 178 | Neu5Acα2-3Galα1-3(Fucα1-4)GlcNAcβ-Sp2 | SiaLe$^a$ |
| 179 | Neu5Acα2-6Galβ1-4GlcNAcβ1-2Manα1-6((Neu5Acα2-6Galβ1-4GlcNAcβ1-2Manα1-6)Manβ1-4GlcNAcβ1-4GlcNAcβ-Sp3 | $A_{di}$ |
| 180 | 3'-O-Su-Galβ1-3(Fucα1-4)GlcNAcβ-Sp2 | 3'-O-su-Le$^a$ |
| 181 | Neu5Acα2-3(6-O-Su)Galβ1-4(Fucα1-3)GlcNAcβ-Sp2 | 6'-sulfo-sLe$^x$ |
| 182 | Neu5Acα2-3Galβ1-4(Fucα1-3)(6-O-Su)GlcNAcβ-Sp2 | 6-sulfo-sLe$^x$ |
| 183 | β-D-Man-Sp2 | β-D-mannose |
| 184 | 9-OS-Sp3 | 9-OS |
| 185 | GalNAcβ1-4(Fucα2)GlcNAcβ1-4Manα1-3(GalNAcβ1-4(Fucα2)GlcNAcβ1-4Manα1-6)Manα1-4GlcNAcβ1-4(Fucα2)GlcNAcβ-N-Sp1 | bi-LDF (modified from human fibrinogen) |
| 186 | Manα1-6(Manα1-3)Manβ1-4GlcNAcβ1-4(Fucα2)GlcNAc-N-Sp1 | Man-3 chitobiose core Fuc (modified from bovine IgG) |
| 187 | Galβ1-4(Fucα1-3)GlcNAcβ1-4Manα1-6(Galβ1-4(Fucα1-3)GlcNAcβ1-4Manα1-6)Manα1-4GlcNAcβ1-4GlcNAcβ-N-Sp1 | desialylated, from fucosylated human apotransferrin |
| 188 | mixed glycans-N-Sp1 | mixed biantennary structures from WeHi cells |

TABLE 1-continued

| | | |
|---|---|---|
| 189 | Manα1-6(Manα1-3)Manα1-6(GlcNAcβ1-4)(GlcNAcβ1-2Manα1-3)Manβ1-4GlcNAcβ1-4GlcNAcβ-N-Sp1 | N-Man5GlcNAc4 (from ovalbumin) |
| 190 | mixed glycans-N-Sp1 | N-glycans from keyhole limpet hemocyanin |
| 191 | Galβ1-4[6-O-Su]Glcβ-Sp1 | 6SuLac |
| 192 | 3-O-Su-Galβ1-4(6-O-Su)Glcβ-Sp1 | 3'6DiSuLac |
| 193 | Galα1-3Galβ1-4Glcβ-Sp1 | Galili-tri |
| 194 | Neu5Acα2-3Galβ1-4GlcNAcβ1-3Galβ1-4GlcNAcβ1-3Galβ1-4GlcNAcβ-Sp1 | 3'SiaLN-LN-LN |
| 195 | Neu5Acα2-3Galβ1-4[Fucα1-3]GlcNAcβ1-3Galβ1-4[Fucα1-3]GlcNAcβ1-3Galβ1-4[Fucα1-3]GlcNAcβ-Sp1 | sLe$^x$-Le$^x$-Le$^x$ |

*Su = sulfate
SPACER ARMS
Code  Spacer Arm

Sp1  —O(CH$_2$)$_2$NHCO(CH$_2$)$_5$NHCO(CH$_2$)$_5$NH-Biotin
Sp2  —O(CH$_2$)$_3$NHCO(CH$_2$)$_5$NH-Biotin
Sp3  —NHCOCH$_2$NH—CO(CH$_2$)$_5$NH-Biotin
Sp4  —O(CH$_2$)$_3$NH—CO(CH$_2$)$_5$NH—CO(CH$_2$)$_5$NH-Biotin
Sp5  —NHCO(CH$_2$)$_5$NHCO(CH$_2$)$_4$NH-Biotin
Sp6  —OCH$_2$CH$_2$CH$_2$NH-Biotin
Sp7  —OCH$_2$CH$_2$NH-Biotin
N    Asparagine
P1   EYEYLDYDFLPETEPPEM
T P1 EYEYTDYDFLPETEPPEM
PAA  Biotinylated polyacrylamide carrier: 20 mol % saccharide, 5 mol % biotin; M$_r$ ~30 kDa Measurement of Siglec-8-Ig Binding Affinity Using Surface Plasmon Resonance (SPR)

All SPR experiments were performed at 25° C. on a Biacore 3000 instrument (Biacore Inc., Piscataway, N.J.). Biotinylated glycosides were captured on research grade streptavidin (SA) coated sensor chips (Sensor Chip SA, Biacore) that were pre-treated according to the manufacturer's instructions. A solution of each biotinylated glycoside (10 fmol/µl) was injected at 2 µl/min in PBS (pH 7.4) containing 0.005% Tween-20 (running buffer) for varying lengths of time (3-7 minutes) until an optimal amount of glycan was captured on each independent surface. Three related glycosides were studied using one SA sensor chip. A control (non-binding) glycan, LacNAc (Galβ1-4GlcNAc), was also captured on the same sensor chip and the specific binding of Siglec-8-Ig for the test glycans was measured using the in-line reference subtraction feature of the Biacore 3000 instrument. Increasing concentrations of Siglec-8-Ig (0.1-18 uM) were injected at a flow rate of 60 µl/min over all four surfaces of the sensor chip. Bound Siglec-8-Ig was found to elute with normal buffer flow after the injection was complete. The equilibrium binding data of Siglec-8-Ig were analyzed by non-linear curve fitting using the BIAevaluation software (Biacore Inc.).

Binding of Siglec-8-Ig to Aminoalkyl Glycosides Immobilized on Activated (N-hydroxysuccinimidyl) Glass Surfaces The N-succinimidyl-activated glass slides (kindly provided by Schott-North America, Duryea, Pa.) were found to be compatible with the consortium library by coupling amino-terminated glycans and is currently being evaluated for a printed version of the consortium glycan array. A description of the printing and evaluation of the full array in this format has been submitted elsewhere (Ola Blixt, Steve Head, Tony Mondala, Christopher Scanlan, Margaret E. Huflejt, Richard Alvarez, Marian C. Bryan, Fabio Fazio, Daniel Calarese, James Stevens, Nahid Razi, David J. Stevens, John J. Skehel, Irma van Die, Dennis Burton, Ian A. Wilson, Richard Cummings, Nicolai Bovin, Chi-Huey Wong, and James C. Paulson (2005) Proc. Natl. Acad. Sci. USA 101, 17033-17038). FITC-labeled goat anti-human IgG (Fc specific) was from Jackson Immunoresearch (West Grove, Pa.).

Aminopropyl glycosides were prepared as described previously (Blixt, O., Collins, B. E., van den Nieuwenhof, I. M., Crocker, P. R., and Paulson, J. C. (2003) J Biol Chem 278, 31007-31019; Galanina, O., Feofanov, A., Tuzikov, A. B., Rapoport, E., Crocker, P. R., Grichine, A., Egret-Charlier, M., Vigny, P., Le Pendu, J., and Bovin, N. V. (2001) Spectrochim Acta A Mol Biomol Spectrosc 57, 2285-2296). Aminohexyl-glucoside was synthesized as described (Barker, R., Chiang, C. K., Trayer, I. P., and Hill, R. L. (1974) Methods Enzymol 34, 317-328).

Aminoalkyl glycosides were covalently immobilized on N-succinimidyl-activated glass (Nexterion Slide H) using the manufacturer's protocols. All procedures were performed at ambient temperature. Briefly, each aminoalkyl glycoside was prepared at a series of concentrations ranging from 0.5 µM to 1 mM in 300 mM sodium phosphate buffer pH 8.5, 0.005% Tween 20 (spotting buffer). Drops (~0.3 µl) of each glycan at each concentration were hand-spotted in quadruplicate on the slide surface in a humid chamber. After spotting, the slide was maintained for an additional hour in the humid chamber, then transferred to a desiccated chamber for 16 h. The slide was then immersed in 50 mM ethanolamine, 50 mM sodium borate (pH 9.0) for 1 h, rinsed with water, dried under a stream of microfiltered air, and stored desiccated.

A solution of 100 µg/ml Siglec-8-Ig and 50 µg/ml FITC-labeled goat anti-human IgG (Fc-specific) in Dulbecco's PBS containing 0.005% Tween 20 was incubated for 30 min at 37° C. to allow complexes to form. The glycan-derivatized slide was immersed in PBS containing 0.01% Tween, drained, and then overlaid with the Siglec-8-Ig-FITC antibody conjugate. After 2 h in a dark humid chamber, the slide was washed by successive immersion in PBS/0.01% Tween (three times) and water/0.01% Tween (twice). The slide was briefly rinsed with distilled water and dried under microfiltered air. An image of the bound fluorescence was obtaining using a microarray scanner (ScanArray Express, PerkinElmer Life Sciences, Boston, Mass.). The integrated spot intensities were determined using Metamorph software (Universal Imaging, Downingtown, Pa.).

Examples

Example 1

Glycan Array Screening

Using the Glycan Array available through the Consortium for Functional Glycomics (http://www.functionalglycomics.org/static/consortium/resources/resourcecoreh.shtml), experiments were initiated to identify compounds that selectively and specifically bind to Siglec-8. Using Siglec-8-Ig fusion protein, a panel of 172 carbohydrate-based structures (see Table 1) was screened for specific Siglec-8 binding. As shown in FIG. 1, Siglec-8-Ig fusion protein had high affinity (12:1 signal-to-noise binding) for structure #181, also know as 6'-sulfo-sLe$^x$ or NeuAcα2-3(6-O-sulfo)Galβ1-4(Fucα1-3)GlcNAcβ1-O(CH$_2$)$_3$NH—CO(CH$_2$)$_5$NH-Biotin (FIG. 2). Of additional particular relevance was that closely related structures to #181, such as structure #182, also known as 6-sulfo-sLe$^x$ NeuAcα2-3 Galβ1-4(Fucα1-3)(6-O-Su) GlcNAcβ1-O(CH$_2$)$_3$NH—CO(CH$_2$)$_5$NH-Biotin, which only differs from structure #181 by the location of the 6-O-sulfate (FIG. 2), and structure #108, also known as sLe$^x$ or NeuAcα2-3Galβ1-4(Fucα1-3)GlcNAcβ1-O(CH$_2$)$_2$NHCO(CH$_2$)$_5$ NHCO(CH$_2$)$_5$NH-Biotin, had minimally increased binding affinity (1.2:1 and 0.8:1 signal-to-noise binding, respectively) for Sigelc-8. The spacer arm itself, —O(CH$_2$)$_3$NH—CO (CH$_2$)$_5$NH-Biotin, found on many of the other non-binding structures, cannot explain the binding activity for Siglec-8. Taken together, this information demonstrates that the 6 position O-linked sulfate on galactose is key to the specificity and affinity of this structure for Siglec-8 (FIG. 2).

Example 2

Validation of Glycan Array Results by SPR

The binding affinities of Siglec-8 for #108, #182 and #181 (FIGS. 3A-C, respectively) were determined on a Biacore B3000 instrument using a streptavidin-coated sensor chip. LacNAc glycoside was captured on one surface of the sensor chip and used as negative control (data not shown). As shown in FIG. 3, Siglec-8 showed specific binding, with very fast association and dissociation profiles only to the ligand #181. The sensorgrams show that upon injection of the Siglec, binding rapidly reaches equilibrium in the first few seconds and the bound Siglec falls off rapidly after the injection is stopped. The apparent Kd for binding of Siglec-8 to ligand #181, was between 2-2.5 μM (FIG. 4).

Example 3

Further Verification of the Glycan Array Results

Binding of Siglec-8-Ig precomplexed with FITC-anti-human Fc to aminopropyl glycosides immobilized on activated (N-hydroxysuccinimidyl) glass surfaces was also used to further verify the specificity of 6'-sulfo-sLe$^x$ as a Siglec-8 ligand. As shown in FIG. 5, fluorescent signals were detected at immobilized concentrations of 6'-sulfo-sLe$^x$ as low as 5 pmol/spot. In contrast, sLe$^x$ and 6-sulfo-sLe$^x$ did not support any Siglec-8 binding at the highest concentration tested (300 pmol/spot).

Sialic acid binding immunoglobulin-like lectin 8 (Siglec-8) is selectively expressed on human eosinophils, basophils, and mast cells, where it regulates their function and survival. Previous studies demonstrated sialic acid-dependent binding of Siglec-8, but failed to reveal significant sub-structure specificity or high affinity of that binding. In an effort to test a broader range of potential ligands, a Siglec-8-Ig chimeric protein was tested for binding to 172 different glycan structures immobilized as biotinylated glycosides on a 384-well streptavidin-coated plate. Of these, ~40 structures were sialylated, including structures with 2-3, 2-6 and 2-8 linked sialic acids in various glycan sequences. Among these, avid binding was detected to a single defined glycan: NeuAcα2-3 (6-O-sulfo)Galβ1-4-[Fucα1-3]GlcNAc, also referred to in the literature as 6'-sulfo-sLe$^x$. Notably, neither unsulfated sLe$^x$ (NeuAcα2-3Galβ1-4-[Fucα1-3]GlcNAc) nor an isomer with the sulfate on the 6-position of the GlcNAc residue (6-sulfo-sLe$^x$, NeuAcα2-3 Galβ1-4-[Fucα1-3](6-O-sulfo) GlcNAc) supported detectable binding. Subsequent secondary screening was performed using surface plasmon resonance. Biotin glycosides immobilized on streptavidin biosensor chips were exposed to Siglec-8-Ig in solution. Whereas surfaces derivatized with sLe$^x$ and 6-sulfo-sLe$^x$ failed to support detectable Siglec-8 binding, 6'-sulfo-sLe$^x$ supported significant binding with a Kd of 2.3 μM. In a separate test of binding specificity, aminopropyl glycosides were covalently immobilized at different concentrations on activated (N-hydroxysuccinimidyl) glass surfaces (Schott-Nexterion Slide H). Subsequent exposure to Siglec-8-Ig precomplexed with FITC-anti-human Fc resulted in fluorescent signals at immobilized concentrations of 6'-sulfo-sLe$^x$ of <5 pmol/spot. In contrast, sLe$^x$ and 6-sulfo-sLe$^x$ did not support any Siglec-8 binding at the highest concentration tested (300 pmol/spot). We conclude that Siglec-8 is a highly specific lectin, binding preferentially to the sLe$^x$ structure bearing an additional sulfate ester on the galactose 6-hydroxyl.

All publications and patent applications disclosed herein are incorporated into this application by reference in their entirety, which can be used in the instant invention.

One skilled in the art will readily appreciate that the present invention is well adapted to carry out the objects and obtain the ends and advantages mentioned, as well as those inherent therein. It will be apparent to those skilled in the art that various modifications and variations can be made in practicing the present invention without departing from the spirit or scope of the invention. Changes therein and other uses will occur to those skilled in the art which are encompassed and equivalent within the spirit of the invention as defined by the scope of the claims.

We claim:

1. The compound NeuAcα2-3(6-O-sulfo)Galβ1-4(Fucα1-3)GlcNAcβ-O—(CH$_2$)$_3$—NH—CO(CH$_2$)$_5$NH-M, where M is a hydrogen or amide linkage; or a pharmaceutically acceptable salt thereof.

2. A pharmaceutical composition comprising any of the compounds of claim 1 and a pharmaceutically acceptable solvent.

3. A method for treating a subject suffering from or susceptible to a disease or disorder involving activation of Siglec-8 on Siglec-8 expressing cells comprising administering to the subject an effective amount of one or more compounds represented by the formula:

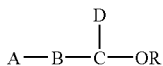

in which
- A is a sialic acid residue or an analog thereof;
- B is a galactose residue or an analog thereof, and is substituted with an anionic moiety at the 6-position;
- C is an N-acetylglucosamine residue or an analog thereof;
- D is a fucose residue or an analog thereof; and
- R together with the O atom to which it is attached, is an aglycone;

or a pharmaceutically acceptable salt thereof.

4. The method of claim 3 wherein the subject is suffering from or susceptible to asthma, allergic diseases, atopic dermatitis, hypereosinophilic syndromes, mastocytosis, leukemias, lymphomas, urticaria, Churg-Strauss syndrome, eosinophilic esophagitis, eosinophilic gastroenteritis, anaphylaxis, and nasal polyposis.

5. The method of claim 3 wherein the subject is a human.

6. A pharmaceutical composition kit comprising i) one or more compounds of claim 1; and ii) directions for use of the one or more compounds of claim 1 to treat a disease or disorder involving activation of Siglec-8 on Siglec-8 expressing cells.

7. A compound represented by the formula:

in which
- A is a sialic acid residue or an analog thereof;
- B is a galactose residue or an analog thereof, and is substituted with an anionic moiety at the 6-position;
- C is an N-acetylglucosamine residue or an analog thereof;
- D is a fucose residue or an analog thereof; and
- wherein R, together with the O atom to which it is attached is an aglycone represented by the structure —O—(CH$_2$)$_3$—NH—CO(CH$_2$)$_5$NH-M, where M is a hydrogen or an amide linkage;

or a pharmaceutically acceptable salt thereof.

8. A compound represented by the formula:

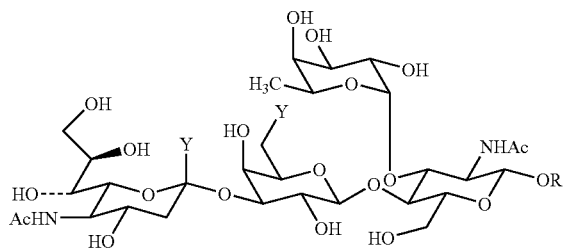

wherein R together with the O atom to which it is attached is an aglycone represented by the structure —O—(CH$_2$)$_3$—NH—CO(CH$_2$)$_5$NH-M, where M is a hydrogen or an amide linkage; and Y is independently for each occurrence an anionic group selected from the group consisting of carboxylate, sulfate, sulfonate, phosphate, phosphonate and hydroxamate;

or a pharmaceutically acceptable salt thereof.

9. The compound of claim 1, wherein the compound binds to Siglec-8 protein with an affinity of less than 10 μM.

10. The compound of claim 7, wherein the compound binds to Siglec-8 protein with an affinity of less than 10 μM.

11. The compound of claim 8, wherein the compound binds to Siglec-8 protein with an affinity of less than 10 μM.

12. A pharmaceutical composition comprising any of the compounds of claim 1, 7, or 8; and a pharmaceutically acceptable solvent.

13. A method for treating a subject suffering from or susceptible to a disease or disorder involving activation of Siglec-8 on Siglec-8 expressing cells comprising administering to the subject an effective amount of one or more compounds of claim 1, 7, or 8.

14. The method of claim 13 wherein the subject is suffering from or susceptible to asthma, allergic diseases, atopic dermatitis, hypereosinophilic syndromes, mastocytosis, leukemias, lymphomas, urticaria, Churg-Strauss syndrome, eosinophilic esophagitis, eosinophilic gastroenteritis, anaphylaxis, and nasal polyposis.

15. The method of claim 13 wherein the subject is a human.

16. A pharmaceutical composition kit comprising
i) one or more compounds of claim 1, 7, or 8; and
ii) directions for use of the one or more compounds of claim 1, 7, or 8 to treat a disease or disorder involving activation of Siglec-8 on Siglec-8 expressing cells.

* * * * *